United States Patent
Rajagopalan et al.

(10) Patent No.: US 7,230,088 B2
(45) Date of Patent: Jun. 12, 2007

(54) COMPOUNDS FOR DUAL PHOTODIAGNOSIS AND THERAPY

(75) Inventors: Raghavan Rajagopalan, Solon, OH (US); Samuel I. Achilefu, St. Louis, MO (US); Joseph E. Bugaj, St. Charles, MO (US); Richard B. Dorshow, St. Louis, MO (US); Muthunadar P. Periasamy, Chesterfield, MO (US)

(73) Assignee: Mallinckrodt, Inc., St. Louis, MO (US)

( * ) Notice: Subject to any disclaimer, the term of this patent is extended or adjusted under 35 U.S.C. 154(b) by 546 days.

(21) Appl. No.: 10/685,172

(22) Filed: Oct. 14, 2003
(Under 37 CFR 1.47)

(65) Prior Publication Data
US 2004/0156783 A1 Aug. 12, 2004

Related U.S. Application Data

(63) Continuation-in-part of application No. 09/898,885, filed on Jul. 3, 2001, now abandoned.

(51) Int. Cl.
*C07K 1/13* (2006.01)
*G01N 33/531* (2006.01)
*G01N 33/533* (2006.01)

(52) U.S. Cl. .......... 530/405; 530/403; 436/546; 436/56; 436/800

(58) Field of Classification Search .......... 436/544, 436/546, 56, 800; 530/403, 405; 543/156
See application file for complete search history.

(56) References Cited
U.S. PATENT DOCUMENTS 3,887,379 A  6/1975  Clecak et al. .......... 95/115 R
3,996,345 A * 12/1976 Ullman et al. .......... 436/537
4,818,684 A *  4/1989 Edelman et al. .......... 435/7.8
5,395,619 A  3/1995  Zalipsky et al. .......... 424/450
5,518,888 A  5/1996  Waldman .......... 435/7.23

(Continued)

FOREIGN PATENT DOCUMENTS

JP  11174672  7/1999

(Continued)

OTHER PUBLICATIONS

Byron Ballou et al., *Tumor labeling in vivo using cyanine-conjugated monoclonal antibodies*, Cancer Immunology and Immunotherapy, vol. 41, 1995, 257-263.

(Continued)

*Primary Examiner*—Long V. Le
*Assistant Examiner*—Shafiqul Haq
(74) *Attorney, Agent, or Firm*—Wood, Herron & Evans LLP

(57) ABSTRACT

The invention discloses compounds and compositions for dual phototherapy and combined therapy and diagnosis of tumors and other lesions. The compounds have a Dye that, when photoactivated, operates via Type I and/or Type II mechanisms. Other Dye or azide components may operate by the same or different mechanisms. Selection of particular components in a compound, and formulation of the compound(s) in a composition permit different activation wavelengths to be used for different therapies. A targeting moiety may be added to the compound or composition so that the Dye locates at a particular site, such as a hormone-sensitive tumor, for diagnosis and/or treatment. The compounds and compositions may be incorporated within liposomes.

7 Claims, 2 Drawing Sheets

U.S. PATENT DOCUMENTS

| | | | |
|---|---|---|---|
| 5,631,018 A | 5/1997 | Zalipsky et al. | 424/450 |
| 5,714,342 A | 2/1998 | Komoriya et al. | 435/23 |
| 6,004,536 A | 12/1999 | Leung et al. | 424/9.6 |
| 6,077,584 A | 6/2000 | Hurditch | 428/64.1 |
| 6,180,085 B1 | 1/2001 | Achilefu et al. | 424/9.6 |
| 6,217,848 B1* | 4/2001 | Achilefu et al. | 424/9.1 |
| 6,258,378 B1 | 7/2001 | Schneider et al. | 424/450 |
| 6,277,403 B1 | 8/2001 | Perez Mendez et al. | 424/450 |
| 6,406,713 B1 | 6/2002 | Janoff et al. | 424/450 |
| 2004/0161430 A1* | 8/2004 | Rajagopalan et al. | 424/178.1 |

FOREIGN PATENT DOCUMENTS

| | | |
|---|---|---|
| WO | WO02089858 | 11/2002 |
| WO | WO03003806 | 1/2003 |
| WO | WO03004091 | 1/2003 |
| WO | WO03004466 | 1/2003 |
| WO | WO03011106 | 2/2003 |
| WO | WO03065888 | 8/2003 |

OTHER PUBLICATIONS

Braun-Falco et al. (Eds.), *Liposome Dermatics*, Griesbach Conference, Springer-Verlag, Berlin 1992).

M.D. Daniel et al., *A History of Photodynamic Therapy*, Aust. N.Z. J. Surg., vol. 61, 1991, 340-348.

T.J. Dougherty et al., *Photoradiation Therapy. II. Cure of Animal Tumors wiht Hematoporphyrin and Light*, Journal of the National Cancer Institute, vol. 55, No. 1, 1975, 115-121.

G. Freiherr, *The Light Stuff: Optical Imaging in Medical Diagnosis*, Medical Device & Diagnostic Industry Magazine, 1998, 40-46.

M.R. Hamblin et al., *On the mechanism of the tumour-localising effect in photodynamic therapy*, J. Photochem. Photobiol. B: Biol., vol. 23, 1994, 3-8.

Hamblin et al., *Targeted photodynamic therapy for infected wounds in mice*, Optical Methods for Tumor Treatment and Detection: Mechanisms and Techniques in Photodynamic Therapy XI (Proceedings of SPIE 2002) pp. 48-58.

J. C. Hebden et al., *Diagnostic Imaging with light*, The British Journal of Radiology, vol. 70, 1997, S206-S214.

D.J. Hnatowich et al., *Radioactive Labeling of Antibody: A Simple and Efficient Method*, Science, vol. 220, 1983, 613-615.

G. Jori, *Far-red-absorbing photosensitizers: their use in the photodynamic therapy of tumours*, J. Photochem. Photobiol. A: Chem., vol. 62, 1992, 371-378.

G. Jori et al., *Second Generation Photosensitizers for the Photodynamic Therapy of Tumours*, Light in Biology and Medicine, vol. 2, R.H. Douglas et al. (Eds.), 1991, 253-266.

G. Jori, *Tumour Photosensitizers: approaches to enhance the selectivity and efficiency of photodynamic therapy*, Journal of Photochemistry and Photobiology B: Biology, vol. 36, 1996, 87-93.

G. Jori, *Novel Therapeutic Modalities Based on Photosensitized Processes*, Journal of Photochemistry and Photobiology B: Biology, No. 60, 1997, 12-18.

M. Korbelik, *Photosensitizers in photodynamic therapy*, Periodicum Biologorum, vol. 93, No. 4, 1991, 563-574.

Lasic & Martin, Eds., *Stealth Liposomes*, 1995, CRC Press, London, pp.

K. Licha et al., *New contrast for optical imaging: acid-cleavable conjugates of cyanine dyes with biomedicals*, In Biomedical Imaging: Reporters, Dyes, and Instrumentation, D.J. Bomhop, C. Contag, and E.M. Servick-Muraca (Eds.), Proceedings of SPIE, vol. 3600, 1999, 29-35.

R.L. Lipson, M.D. et al., *Hematoporphyrin Derivative for Detection and Management of Cancer*, Cancer, vol. 20, No. 12, 1967, 2255-2257.

Y. Luo et al., *Rapid Initiation of Apoptosis by Photodynamic Therapy*, Photochemistry and Photobiology, vol. 63, No. 4, 1996, 528-534.

K. Matsumura, *1-Aminoacridine-4-carboxylic Acid*, Journal of the American Chemical Society, vol. 60, (1938) 591-593.

G.G. Miller et al., *Preclinical assessment of hypocrellin B and hypocrellin B derivatives as sensitizers for photodynamic therapy of cancer: progress update*, Photochemistry and Photobiology, vol. 65, No. 4, 1997, 714-722.

I. Ol'shevskaya, *Cyanine dyes from azidobenzothiazole and benzimidazole*, Chem. Ab. No. 1974:522571.

T. Parasassi et al., *Two-photon microscopy of aorta fibers shows proteolysis induced by LDL hydroperoxides*, Free Radical in Biology and Medicine, vol. 28, No. 11, 2000, 1589-1597.

D.J. Pasto et al., *Demonstration of the Synthetic Utility of the Generation of Alkoxy Radicals by the Proto-Induced, Homolytic Dissociation of Alkyl 4-Nitrobenzenesulfenates*, Tetrahedron Letters, vol. 35, No. 25, 1994, 4303-4306.

Patonay et al., *Near-Infrared Fluorogenic Labels: New Approach to and Old Problem*, Anal. Chem., 63:6 (1991) pp. 321A-327A.

A. Pelegrin et al., *Photoimmunodiagnosis with antibody-fluorescein conjugates: in vitro and in vivo preclinical studies*, J. Cell Pharmacol, vol. 3, 1992, 141-145.

V. Pochinok et al., *Photochemistry of azide group containing dyes in solution*, Chem. Ab. No. 1984:439817.

Paras N. Prasad, *Light-Activated Therapy: Photodynamic Therapy*, Introduction to Biophotonics, 2003, J. Wiley & Sons, pp. 433-463.

W. G. Roberts et al., *Role of Neovasculature and Vascular Permeability on the Tumor Retention of Photodynamic Agents*, Cancer Research, vol. 52, 1992, 924-930.

G.I. Stables et al., *Photodynamic therapy*, Cancer Treatment Reviews, vol. 21, 1995, 311-323.

S. Sunthankar et al., *Reactive disperse dyes, 1, Reactivity involving nitrene intermediate from azido group*, Indian Journal of Chemistry, 1974 11(5):503-504.

T. Takemura et al., *Mechanism of Photodynamic Therapy: Exploration by Photophysiocochemical Study*, Frontiers of Photobiology, 1993, 503-506.

K.B. Trauner et al., *Photodynamic Synovectomy Using Benzoporphyrin Derivative in an Antigen-Induced Arthritis Model for Rheumatoid Arthritis*, Photochemistry and Photobiology, vol. 67, No. 1, 1998, 133-139.

P.J. van Geel et al., *Photosensitizing Efficacy of MTHPC-PDT Compared to Photofrin-PDT in the RIF1 Mouse Tumour and Normal Skin*, Int. J. Cancer, vol. 60, 1995, 388-394.

JE van Lier et al., *The chemistry, photophysics, and photosensitizing properties of phthalocyanines*, Photosensitizing Compounds: Their Chemistry, Biology, and Clinical Use (Ciba Foundation Symposium 146), Bock and Hamett, Eds., J. Wiley & Sons, 1989, pp. 17-32.

EPO, *Supplementary Partial European Search Report*, EP02749597, 8 pg.

PCT, *International Search Report*, PCT/US2004/032859, International filing date Oct. 7, 1004, 5 pg.

Rajagopalan et al., *Targeted Type 1 phototherapeytic agents using azido-peptide bioconjugates*, Proceedings of SPIE, 2001, vol. 4529: 129-132.

\* cited by examiner

COMPOUNDS FOR DUAL PHOTODIAGNOSIS AND THERAPY

CROSS-REFERENCE TO RELATED APPLICATIONS

This application is a Continuation-In-Part of U.S. patent application Ser. No. 09/898,885, filed on Jul. 3, 2001, now abandoned, the disclosure of which is hereby incorporated by reference in its entirety.

FIELD OF THE INVENTION

The invention relates generally to novel compounds useful for dual photodiagnostic and phototherapeutic procedures.

BACKGROUND OF THE INVENTION

The use of visible and near-infrared (NIR) light in clinical practice is growing rapidly. Compounds absorbing or emitting in the visible or NIR, or long-wavelength (UV-A, >350 nm) region of the electromagnetic spectrum are potentially useful for optical tomographic imaging, endoscopic visualization, and phototherapy. However, a major advantage of biomedical optics lies in its therapeutic potential. Phototherapy has been demonstrated to be a safe and effective procedure for the treatment of various surface lesions, both external and internal. Its efficacy is akin to radiotherapy, but it advantageously lacks the harmful radiotoxicity to critical non-target organs.

Phototherapy has been in existence for many centuries and has been used to treat various skin surface ailments. As early as 1400 B.C. in India, plant extracts (psoralens), in combination with sunlight, were used to treat vitiligo. In 1903, Von Tappeiner and Jesionek used eosin as a photosensitizer for treating skin cancer, lupus of the skin, and condylomata of female genitalia. Over the years, the combination of psoralens and ultraviolet A (low-energy) radiation has been used to treat a wide variety of dermatological diseases and manifestations including psoriasis, parapsoriasis, cutaneous T-cell lymphoma, eczema, vitiligo, areata, and neonatal bilirubinemia. Although the potential of cancer phototherapy has been recognized since the early 1900's, systematic studies to demonstrate safety and efficacy began only in 1967 with the treatment of breast carcinoma. In 1975, Dougherty et al. conclusively established that long-term cure is possible with photodynamic therapy (PDT). Currently, phototherapeutic methods are also being investigated for the treatment of some cardiovascular disorders such as atherosclerosis and vascular restenosis, for the treatment of rheumatoid arthritis, and for the treatment of some inflammatory diseases such as Crohn's disease.

Phototherapeutic procedures require photosensitizers (i.e. chromophores) having high absorptivity. These compounds should preferably be chemically inert, and become activated only upon irradiation with light of an appropriate wavelength. Selective tissue injury can be induced with light when photosensitizers bind to the target tissues, either directly or through attachment to a bioactive carrier. Furthermore, if the photosensitizer is also a chemotherapeutic agent (e.g., anthracycline antitumor agents), then an enhanced therapeutic effect can be attained. An effective phototherapeutic agent should include the following: (a) large molar extinction coefficients, (b) long triplet lifetimes, (c) high yields of singlet oxygen and/or other reactive intermediates, viz., free radicals, nitrenes, carbenes, or open-shell ionic species such as cabonium ions and the like, (d) efficient energy or electron transfer to cellular components, (e) low tendency to form aggregation in an aqueous milieu, (f) efficient and selective targeting of lesions, (g) rapid clearance from the blood and non-target tissues, (h) low systemic toxicity, and (i) lack of mutagenicity.

Photosensitizers operate via two distinct mechanisms, termed Types 1 and 2. The Type 1 mechanism is shown in the following scheme:

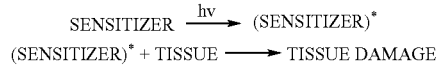

Type 1 mechanisms involve direct energy or electron transfer from the photosensitizer to the cellular components thereby causing cell death. Type 2 mechanisms involve two distinct steps, as shown in the following scheme:

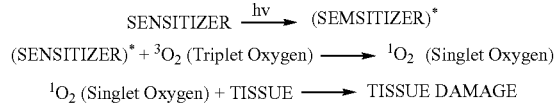

In the first step, singlet oxygen is generated by energy transfer from the triplet excited state of the photosensitizer to the oxygen molecules surrounding the tissues. In the second step, collision of singlet oxygen with the tissues promotes tissue damage. In both Type 1 and Type 2 mechanisms, the photoreaction proceeds via the lowest triplet state of the sensitizer. Hence, a relatively long triplet lifetime is required for effective phototherapy. In contrast, a relatively short triplet lifetime is required to avoid photodamage to the tissue caused by photosensitizers.

The biological basis of tissue injury brought about by tumor phototherapeutic agents has been the subject of intensive study. Various biochemical mechanisms for tissue damage have been postulated even though the type and number of photosensitizers employed in these studies are relatively small. These biochemical mechanisms are as follows: (a) cancer cells upregulate the expression of low density lipoprotein (LDL) receptors, and photodynamic therapy (PDT) agents bind to LDL and albumin selectively; (b) porphyrin-like substances are selectively taken up by proliferative neovasculature; (c) tumors often contain increased number of lipid bodies and are thus able to bind to hydrophobic photosensitizers; (d) a combination of "leaky" tumor vasculature and reduced lymphatic drainage causes porphyrin accumulation; (e) tumor cells may have increased capabilities for phagocytosis or pinocytosis of porphyrin aggregates; (f) tumor associated macrophages may be largely responsible for the concentration of photosensitizers in tumors; and (g) cancer cells may undergo apoptosis induced by photosensitizers. Among these mechanisms, (f) and (g) are the most general and, of these two alternatives, there is a general consensus that (f) is the most likely mechanism by which the phototherapeutic effect of porphyrin-like compounds is induced.

Most of the currently known photosensitizers are commonly referred to as PDT agents and operate via the Type 2 mechanism. For example, Photofrin II (a hematoporphyrin derivative) has been recently approved by the United States Food and Drug Administration for the treatment of bladder, esophageal, and late-stage lung cancers. However, Photofrin II has been shown to have several drawbacks: a low molar absorptivity ($\epsilon$=3000 M$^{-1}$), a low singlet oxygen quantum yield ($\Phi$=0.1), chemical heterogeneity, aggregation, and prolonged cutaneous photosensitivity. Hence, there has been considerable effort in developing safer and more effective photosensitizers for PDT which exhibit improved light absorbance properties, better clearance, and decreased skin photosensitivity compared to Photofrin II. These include monomeric porphyrin derivatives, corrins, cyanines, phthalocyanines, phenothiazines, rhodamines, hypocrellins, and the like. However, these phototherapeutic agents also mainly operate via the Type 2 mechanism.

Surprisingly, there has not been much attention directed at developing Type 1 phototherapeutic agents, despite the fact that the Type 1 mechanism appears to be inherently more efficient than the Type 2 mechanism. First, unlike Type 2, Type 1 photosensitizers do not require oxygen for causing cellular injury. Second, the Type 1 mechanism involves two steps (photoexcitation and direct energy transfer), whereas the Type 2 mechanism involves three steps (photoexcitation, singlet oxygen generation, and energy transfer). Furthermore, certain tumors have hypoxic regions, which renders the Type 2 mechanism ineffective. However, in spite of the drawbacks associated with the Type 2 mechanism, only a small number of compounds have been developed that operate through the Type 1 mechanism, e.g. anthracyline antitumor agents.

Thus, there is a need to develop more effective phototherapeutic agents.

SUMMARY OF THE INVENTION

Agents for dual phototherapy having the general formula E-L-DYE-X—$N_3$ (compound 1) and/or E-L-DYE-X—Y (compound 2) are disclosed. These include compositions containing one or more of these Dye-containing compounds that, when photoactivated, damage tissues containing these compounds by a Type I mechanism, a Type II mechanism, or combined Type I/Type II mechanisms.

The invention includes the compounds themselves, It also includes physiologically acceptable compositions of the compounds, defined as formulations of the compounds for administration by any route to living cells in vivo or in vitro. It also includes methods for phototherapy by administering and photoactivating the compositions. Each of these will be described in detail.

The compositions may be prepared such that the photoactivated compound(s) at a tumor or other site can act by Type I, Type II, or combined Type I/Type II mechanisms. Many formulations are possible; for example and as will be further described, a composition may have both Type I and Type II components in the same compound; it may have both Type I and Type II components in a mixture containing different compounds; it may have two Type I components in the same compound or in a mixture containing different compounds; or it may have two Type II components in the same compound or in a mixture containing different compounds.

The photoactive components are Dye, Y, and azide ($N_3$), with the Dye and Y components generally containing large cyclic or aromatic rings. The Dye is linked a to moiety, designated generally as E, which can be selected to target the compound to a specific site or which can be hydrogen. The Dye is also linked to another photoactive component (either $N_3$ in compound 1, or the general designation Y in compound 2) that, when photoactivated, additionally damages tissues via either a Type I mechanism or a Type II mechanism. It will be appreciated that, by selecting specific components for each of Dye and Y, one can select for either Type 1 and/or Type II mechanisms of photoactivation (photodiagnosis and/or phototherapy). It will also be appreciated that, by selecting specific components for E, one can target the compound or composition to reach a specific body site, for example, a tumor site where photoactivation will destroy tumor cells. It will also be appreciated that the linking components can be selected to space the bulky Dye and Y structures.

Depending upon the identity of the Dye and Y selected, and the presence or absence of $N_3$, various compositions are possible and are included within the scope of the invention. For example, the composition or formulation may contain, within a single compound, one component activated by a Type I mechanism and another component activated by a Type II mechanism. Alternatively, the composition or formulation may contain at least two compounds, where each compound, when activated, acts via a Type I mechanism, or a Type II mechanism, or where at least one compound acts via a Type I mechanism and at least one other compound acts via a Type II mechanism.

It will be appreciated that numerous combinations of photoactive components (Dye, Y, and $N_3$) are possible to provide a desired mechanism of action, as will be described. Additionally, it will be appreciated that many formulations are possible because of the various linkers and targeting moieties that may be used, as will also be described. As used herein, a formulation or composition refers to a pharmaceutically acceptable formulation that is administered to a patient. Thus, as has been described, a formulation may be a single compound containing both Type I and Type II functional groups, or at least two compounds.

In one embodiment, a formulation further includes a liposome as a carrier or vehicle for the compound(s). The Dye and/or Y component is a part of the lipophilic bilayers, and the targeting moiety, if present (that is, if E is not hydrogen), is on the external surface of the liposome. Alternatively, a targeting moiety can be externally attached to the liposome after formulation for targeting the liposome-containing inventive compound to the desired site.

The compositions can be used for photodiagnosis, phototherapy, or combined photodiagnosis and phototherapy. In the latter embodiment, the composition is administered and photoactivated at the appropriate wavelength to verify the location of the compound at a specific site (e.g., a tumor site). Upon verification (photodiagnosis), the compound is photoactivated at the appropriate wavelength to destroy the cells or tissues in the region of the compound (phototherapy).

The novel compositions are used for phototherapy of tumors and other lesions. The formulations can also be used in a combined photodiagnostic and phototherapeutic procedure where, after administering the formulation to the patient, the photodiagnostic part of the procedure is performed followed by the phototherapeutic part.

In one embodiment, the invention discloses one or more compounds having the general formula 1

The Dye is any of cyanines, phthalocyanines, porphyrins, indocyanines, rhodamines, phenoxazines, phenothiazines, phenoselenazines, fluoresceins, benzoporphyrins, squaraines, corrins, croconiums, chalcogenopyrylium analogues, non-cationic dyes attached to polycationic peptides, chlorins, naphthalocyanines, cationic dyes, methine dyes, and indolenium dyes, all of which operate via a Type II mechanism. The Dye may also be a peroxide, a sulfenate, an azo, a diazo, an anthracycline, or a derivative or class thereof; all of which operate via a Type I mechanism. Phenoxazines, phenothiazines, and phenoselenazines may also operate via a Type I mechanism. As used herein, Dye encompasses the parent compound itself, as well as any aromatic or heteroaromatic radical derived from the parent, as well as any members in the same class as the parent compound.

The azide ($N_3$) component is activated via a Type I mechanism. Thus, in this embodiment, the compound of formula 1 can be the single compound for dual phototherapy (that is, containing both Type I and Type II components within a single compound). In this embodiment, the compound of formula 1 may be a mixture of two or more compounds containing both Type I and Type II components in two different compounds. In this embodiment, the compound of formula 1 may be a mixture of two or more compounds containing only Type I agents, and, for example, an azo Dye providing another Type I mechanism of action. The presence of the azide in formula 1 will provide a Type I mechanism of action. By providing a formulation containing compounds having the desired Dyes, the mechanism of operation of the formulation can be predetermined.

In an alternative embodiment, the invention discloses compounds having the general formula 2

E-L-DYE-X—Y the Dye and Y may be any of the compounds disclosed for formula 1. In addition, Y may be hydrogen, halogens, anthracylines, azide, C1–C20 peroxyalkyl, C1–C20 peroxyaryl, C1–C20 sulfenatoalkyl, sulfenatoaryl, an aromatic or a heteroaromatic radical derived from or in the class of any of cyanines, phthalocyanines, porphyrins, indocyanines, rhodamines, phenoxazines, phenothiazines, phenoselenazines, fluoresceins, benzoporphyrins, squaraines, corrins, azo dyes, diazo dyes, croconiums, chalcogenopyrylium analogues, non-cationic dyes attached to polycationic peptides; chlorines, naphthalocyanines, non-cationic dyes attached to polycationic peptides, cationic dyes, methine dyes, and indolenium dyes.

In this embodiment, various combinations are possible. For example, in one compound, the Dye and Y components may both act via a Type I mechanism, or may both act via a Type II mechanism, or one may act by a Type I mechanism (Dye or Y), and the other may act by a Type II mechanism. As another example, the formulation may contain at least two compounds. In one compound, the Dye and Y components may both act via a Type I mechanism, while in the other compound, the Dye and Y components may both act via a Type II mechanism. Alternatively, in one compound, one component may act by either a Type I or Type II mechanism, with the other component in that compound of a different Type, and both components in the other compound may be the same or different. In addition, Formula 2 compounds where Y is a Dye can function both as a diagnostic agent as well as a therapeutic agent.

In other alternatives of this embodiment of Formula 2, Y may be hydrogen. If a Dye is selected that acts via a Type I mechanism and no other photoactive compound is present, the composition will act via a Type I mechanism. If the Dye is selected that acts via a Type II mechanism and no other photoactive compound is present, the composition will act via a Type II mechanism. If at least one other photoactive compound is present, Y may also be hydrogen or may be any of the dyes previously described.

For either Formula 1 or Formula 2 compounds, E may be either hydrogen or a targeting moiety. A targeting moiety includes but is not limited to one or more specific sites of a molecule which will bind to a particular complementary site, such as the specific sequence of amino acids in a region of an antibody that binds to the specific antigen binding site. As used in the present invention, the targeting moiety is not limited to a particular sequence or site, but includes anything that will target the inventive compound and/or composition to a particular anatomical and/or physiological site. Examples of compounds that may be used as a targeting moiety for E in the above formulas 1 and 2 include somatostatin receptor binding molecules, heat sensitive bacterioendotoxin receptor binding molecules, neurotensin receptor binding molecules, bombesin receptor binding molecules, cholecystekinin receptor binding molecules, steroid receptor binding molecules, and carbohydrate receptor binding molecules.

The linker L in either Formula 1 or Formula 2 is selected from the group of —$(CH_2)_a$—, —$(CH_2)_b$ $CONR^1$—, —$N(R^2)CO(CH_2)_c$—, —$OCO(CH_2)_d$—, —$(CH_2)_eCO_2$—, —OCONH—, —$OCO_2$—, —HNCONH—, —HNCSNH—, —HNNHCO—, —$OSO_2$—, —$NR^3(CH_2)_e$ $CONR^4$—, —$CONR^5(CH_2)_fNR^6CO$—, and —$NR^7CO$ $(CH_2)_gCONR^8$—, X is either a single bond or is selected from the group of —$(CH_2)_h$—, —OCO—, —HNCO—, —$(CH_2)_iCO$—, and —$(CH_2)_jOCO$—; $R^1$ to $R^8$ are independently selected from the group of hydrogen, C1–C10 alkyl, —OH, C1–C10 polyhydroxyalkyl, C1–C10 alkoxyl, C1–C10 alkoxyalkyl, —$SO_3H$, —$(CH_2)_kCO_2H$, and —$(CH_2)_lNR^9R^{10}$. $R^9$ and $R^{10}$ are independently selected from the group consisting of hydrogen, C1–C10 alkyl, C5–C10 aryl, and C1–C10 polyhydroxyalkyl; and a to l independently range from 0 to 10.

The invention also discloses a method of performing a therapeutic procedure using the inventive compounds. An effective amount of a formulation containing at least two compounds of formula 1,

E-L-DYE-X—$N_3$ formula 2,

E-L-DYE-X—Y or a combination of formulas 1 and 2 where the definitions of E, L, Dye, X, and Y are as previously described, is administered to a subject. Following administration, the photosensitizer, if targeted, is allowed to accumulate in target tissue which is exposed to a light having a wavelength that will allow the excited state of the compound to directly damage the target tissue. For example, activation may be with sufficient power and fluence rate to cause necrosis or apoptosis of the target tissue.

The particular wavelength required for photoactivation to achieve a specific mechanism of action with a specific composition may be determined in a variety of ways. As one example, it may be determined empirically from exposing the synthesized compound to light of varying wavelength and thereafter assaying to determine the extent of tissue damage at a targeted site. It may also be determined based upon the known photoactivation maxima for the particular components selected for Dye and Y. In general, agents that act via a Type I mechanism can be activated across a wide wavelength spectrum from about 300 nm to about 950 nm.

Thus, activation of a Type I component or composition may be achieved using an activation wavelength in this range. In general, agents that act via a Type II mechanism can be activated by light in the range between about 600 nm to about 800 nm in one embodiment, in the range between about 600 nm to about 700 nm in another embodiment, in the range between about 600 nm to about 675 nm in another embodiment, in the range between about 625 nm to about 675 nm in another embodiment, and at around 650 nm in another embodiment. In one embodiment azine compounds (e.g., phenoxazines, phenothiazines, phenoselenazines) may operate via a Type I mechanism and are photoactivated at wavelengths up to about 950 nm, but may also absorb at lower wavelengths, for example, in the range between about 600 nm to about 700 nm. This renders azide compounds capable of operating via a Type I mechanism when higher wavelengths are selected for activation, and also operating via a Type II mechanism when a wavelength in the range between about 600 nm to about 700 nm is selected for activation.

In an alternative embodiment of the inventive method, the compositions are used to perform a phototherapeutic and/or a photodiagnostic procedure. A formulation is prepared using any of the compounds previously described, along with excipients, buffers, etc. to provide a composition for administration by any one of a variety of routes. The composition may be injected, ingested, applied topically, administered by aerosol formulation or inhalation, etc. After administration, the composition accumulates, for example, at a target tissue if a targeting moiety is included in the compound. The selected target site, or a site requiring diagnosis or treatment, is exposed to light with a sufficient power and fluence rate to render a diagnosis and/or treatment. In the embodiment where at least two formula 2 compounds are administered as a composition, the Dye may be selected such that one compound is a diagnostic agent and the other compound is a therapeutic agent.

Porphyrins are examples of photoactive agents used in photodynamic therapy. Protoporphyrin is also a good photosensitizing agent; protoporphyrin IX is a photoactive compound which is endogenously formed from 5-aminolevulinic acid (ALA) in the biosynthetic pathway of heme. ALA may be applied topically and is metabolized to protoporphyrin, the active photosensitizing agent. Irradiation may be at a wavelength in the range of about 630 nm, or alternatively in the range of about 670 nm. Other photosensitizing agents that may be used include, but are not limited to, benzoporphyrin derivative monoacid tube A (BPD-MA) and mono-l-aspartyl chlorine 6 (NPe6), with absorbance maxima in the range of about 660–690 nm, ATX-106, and indocyanine green (ICG). Another photosensitive agent that may be used is verteporfin, a synthetic, chlorin-like porphyrin. It may be activated at a wavelength of around 689 nm. Once activated, it generates singlet oxygen and other reactive oxygen radicals that selectively damage tissues.

A composition may be prepared that contains two formula 2 compounds and thus the composition may function as a dual functional agent as well as a dual phototherapy agent. That is, the composition has one formula 2 compound with a component capable of photodiagnosis, with the other formula 2 compound having a component capable of phototherapy. For example, a phototherapeutic Dye in one compound may be a member of the porphyrin class of compounds, or a member of the phenoxazine, phenothiazine, etc. class of compounds. This compound of the composition will provide phototherapy upon activated, as described using porphyrins as a representative but non-limiting example. The Dye in the other compound may be a member of the cyanine, indocynanine, fluorescein, etc. class of compounds. This compound of the composition, as a diagnostic agent, two compounds of formula 2 are used. The compound of formula 2 may contain a porphyrin Dye, and a non-porphyrin component Y.

These and other advantages and embodiments of the inventive compounds and methods will be apparent in view of the following Figures, description, and examples.

DETAILED DESCRIPTION OF THE INVENTION

Figure 1:
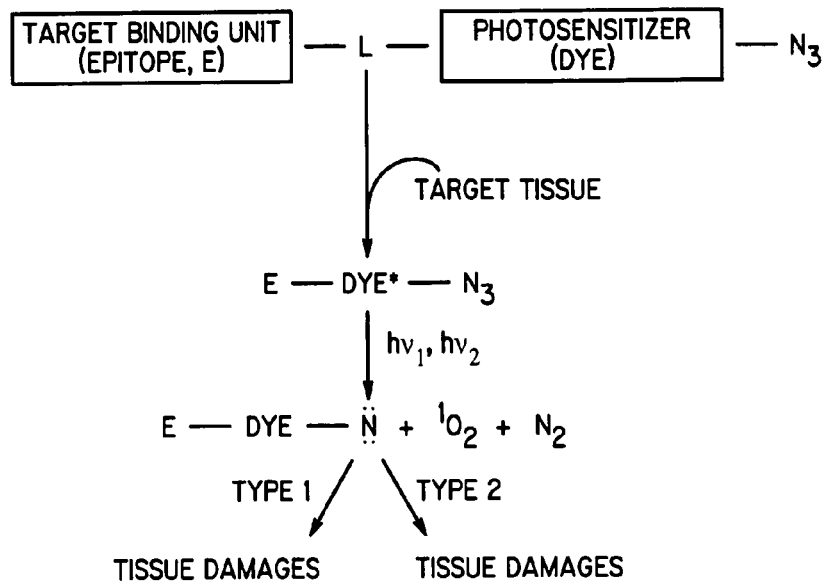
FIG. 1 is a schematic mechanism for activation of the inventive compounds.

The invention discloses compounds with a Dye component that can be photoactivated to form reactive species that will destroy tissue by either a Type I mechanism or a Type II mechanism. The invention also discloses compositions or formulations containing at least two of these compounds that, when administered to a patient and photoactivated, will destroy tissue by either or both Type I and Type II mechanisms, depending upon the specific Dye selected in the compound and/or upon the activation wavelength. The compounds may contain a targeting moiety that may contain one or more epitopes and targets the compound to a specific physiological or anatomical site for site-specific phototherapy. These may be used for phototherapy of tumors and other lesions, or used in the photodiagnosis of tumors and other lesions sequentially followed by phototherapy of the tumors in an appropriate amount of time before the bioconjugate clears from the site. In this example, the composition desirably needs only to be administered once to the patient. The compounds and compositions of formula 1 and formula 2 may synthesized using methods known to one skilled in the art.

Dual phototherapy may be classified into four distinct modes: (a) a composition of at least two different Type 1 compounds; (b) a composition of at least two different Type 2 compounds; (c) a composition of at least one Type 1 compound and one Type 2 compound; and (d) a single compound that contains both Type 1 and Type 2 functionalities. Differences can be in any of the parts of the compound, namely, E, L, X, DYE or Y.

In one embodiment, the invention discloses one or more of compound 1

E-L-DYE-X—$N_3$

The Dye is any of cyanines, phthalocyanines, porphyrins, indocyanines, rhodamines, phenoxazines, phenothiazines, phenoselenazines, fluoresceins, benzoporphyrins, squaraines, corrins, croconiums, chalcogenopyrylium analogues, chlorins, naphthalocyanines, non-cationic dyes attached to polycationic peptides, cationic dyes, methine dyes, and indolenium dyes. The Dye may also be a peroxide, a sulfenate, an azo, a diazo, an anthracycline, or a derivative or class thereof; all of which operate via a Type I mechanism. Phenoxazines, phenothiazines, and phenoselenazines may also operate via a Type I mechanism. As used herein, Dye encompasses the parent compound itself, as well as any aromatic or heteroaromatic radical derived from the parent, as well as any members in the same class as the parent compound.

The azide ($N_3$) component is activated via a Type I mechanism. Thus, in this embodiment, compound 1 can be a single compound for dual phototherapy (that is, containing both Type I and Type II components within the same compound). It can also be two or more compounds containing both Type I and Type II components in two different compounds. It can also be two or more compounds containing only Type I agents with $N_3$ also providing a Type I mechanism of action. By selecting the specific compound, and by selecting the specific Dye and/or Y in each compound, the mechanism of action of the composition can be predetermined.

In an alternative embodiment, the invention discloses one or more of compound 2

E-L-DYE-X—Y

The identity of the Dye and Y components may be any of the compounds disclosed for formula 1. In addition, Y may be hydrogen, halogens, anthracylines, azides, C1–C20 peroxyalkyl, C1–C20 peroxyaryl, C1–C20 sulfenatoalkyl, sulfenatoaryl, an aromatic or a heteroaromatic radical derived from or in the class of any of cyanines, phthalocyanines, porphyrins, indocyanines, rhodamines, phenoxazines, phenothiazines, phenoselenazines, fluoresceins, benzoporphyrins, squaraines, corrins, azo dyes, diazo dyes, croconiums, chalcogenopyrylium analogues, non-cationic dyes attached to polycationic peptides, chlorins, cationic dyes, methine dyes, and indolenium dyes.

In this embodiment, various combinations are possible. For example, in one compound, the Dye and Y components may both act via a Type I mechanism, or may both act via a Type II mechanism, or one may act by a Type I mechanism (Dye or Y), and the other may act by a Type II mechanism. As another example, the formulation may contain at least two compounds. In one compound, the Dye and Y components may both act via a Type I mechanism, while in the other compound, the Dye and Y components may both act via a Type II mechanism. Alternatively, in one compound, one component may act by either a Type I or Type II mechanism, with the other component in that compound of a different Type, and both components in the other compound may be the same or different. In addition, compound 2 where Y is a Dye can function both as a diagnostic agent as well as a therapeutic agent.

In other alternatives of this embodiment of compound 2, Y may be hydrogen. If a Dye is selected that acts via a Type I mechanism and no other compound is present, the composition will act via a Type I mechanism. If the Dye is selected that acts via a Type II mechanism and no other compound is present, the composition will act via a Type II mechanism. If at least one other compound is present, Y may also be hydrogen or may be any of the dyes previously described.

For either Formula 1 or Formula 2 compounds, E may be either hydrogen or a moiety that targets the compound to a particular anatomic and/or physiologic site. Such a targeting moiety includes, but is not limited to, one or more specific sites of a molecule which will bind to a particular complementary site. One example is a specific sequence of amino acids in a region of an antibody that binds to the specific antigen binding site. As used in the present invention, the targeting moiety is not limited to a particular sequence or site, but includes anything that will target the inventive compound and/or composition to a particular anatomical and/or physiological site. While it is not limited to an entire biomolecule such as a protein or a peptide, it may include the entire molecule and, as such, is said to be associated with a biomolecule. Examples of compounds that may be used as a targeting moiety for E in compounds I and II include somatostatin receptor binding molecules, heat sensitive bacterioendotoxin receptor binding molecules, neurotensin receptor binding molecules, bombesin receptor binding molecules, cholecystekinin receptor binding molecules, steroid receptor binding molecules, and carbohydrate receptor binding molecules.

The linking component L between the Dye and E in either compound 1 or compound 2 is selected from the group of —$(CH_2)_a$—, —$(CH_2)_b CONR^1$—, —$N(R^2)CO(CH_2)_c$—, —$OCO(CH_2)_d$—, —$(CH_2)_e CO_2$—, —OCONH—, —$OCO_2$—, —HNCONH—, —HNCSNH—, —HNNHCO—, —$OSO_2$—, —$NR^3(CH_2)_e CONR^4$—, —$CONR^5(CH_2)_f NR^6 CO$—, and —$NR^7 CO(CH_2)_g CONR^8$—. The linking component X between the Dye and $N_3$ (compound 1) or Y (compound 2) is either a single bond or is selected from the group of —$(CH_2)_h$—, —OCO—, —HNCO—, —$(CH_2)_i CO$—, and —$(CH_2)_j OCO$—. $R^1$ to $R^8$ are independently selected from the group of hydrogen, C1–C10 alkyl, —OH, C1–C10 polyhydroxyalkyl, C1–C10 alkoxyl, C1–C10 alkoxyalkyl, —$SO_3H$, —$(CH_2)_k CO_2H$, and —$(CH_2)_l NR^9 R^{10}$. $R^9$ and $R^{10}$ are independently selected from the group consisting of hydrogen, C1–C10 alkyl, C5–C10 aryl, and C1–C10 polyhydroxyalkyl; and a to l independently range from 0 to 10.

The invention also discloses a method of performing a photoactive procedure using the inventive compounds. An effective amount of a formulation containing at least two of compound 1,

E-L-DYE-X—$N_3$ at least two of compound 2,

E-L-DYE-X—Y or a combination of compounds 1 and 2 where the definitions of E, L, Dye, X, and Y are as previously described, is administered to a subject. Following administration, the photosensitizer, if targeted, is allowed to accumulate in target tissue which is exposed to a light having a wavelength that will allow the excited state of the compound to directly damage the target tissue. For example, activation may be with sufficient power and fluence rate to cause necrosis or apoptosis of the target tissue.

The particular wavelength or range required for photoactivation to achieve a specific mechanism of action with a specific composition may be determined in a variety of ways. As one example, it may be determined empirically from exposing the synthesized compound to light of varying wavelength and thereafter assaying to determine the extent of tissue damage at a targeted site. It may also be determined based upon the known absorbance maxima for the particular components selected for Dye and Y. In general, agents that act via a Type I mechanism can be activated across a wide wavelength spectrum, for example, from about 300 nm to about 950 nm, or from about 700 nm to about 950 nm. Thus, activation of a Type I component or composition may be achieved by using an activation wavelength in this range. In general, agents that act via a Type II mechanism can be activated by light in the range between about 600 nm to about 800 nm in one embodiment, in the range between about 600 nm to about 700 nm in another embodiment, in the range between about 600 nm to about 675 nm in another embodiment, and at around 650 nm in another embodiment. In one embodiment, azine compounds (e.g., phenoxazines, phenothiazines, phenoselenazines) may operate via a Type I mechanism and are photoactivated at wavelengths up to about 950 nm, but may also absorb at lower wavelengths, for example, in the range between about 600 nm to about 700 nm. This renders azine compounds capable of operating via a Type II mechanism if they absorb in the range between about 600 nm to about 700 nm, or by a Type I mechanism when other wavelenghts are chosen.

In an alternative embodiment of the inventive method, the compositions are used to perform a phototherapeutic and/or a photodiagnostic procedure. A formulation is prepared using any of the compounds previously described, along with excipients, buffers, etc., to provide a composition for administration by any one of a variety of routes. The composition may be injected, ingested, applied topically, transdermally, subcutaneously, administered by aerosol formulation or inhalation, etc. After administration, the composition accumulates, for example, at a target tissue if a targeting moiety is included in the compound. The selected target site, or a site requiring diagnosis or treatment, is exposed to light with a sufficient power and fluence rate to render a diagnosis and/or treatment. In the embodiment where at least two of compound 2 are administered in a composition, the Dye may be selected such that one compound is a diagnostic agent and the other compound is a therapeutic agent.

Porphyrins are examples of photoactive agents used in photodynamic therapy, Protoporphyrin is also a good photosensitizing agent; protoporphyrin IX is a photoactive compound which is endogenously formed from 5-aminolevulinic acid (ALA) in the biosynthetic pathway of heme. ALA may be applied topically and is metabolized to protoporphyrin, the active photosensitizing agent. Irradiation may be at a wavelength in the range of about 630 nm, or alternatively in the range of about 670 nm. Other photosensitizing agents that may be used include, but are not limited to, benzoporphyrin derivative monoacid tube A (BPD-MA) and mono-l-aspartyl chlorine 6 (NPe6), with absorbance maxima in the range of about 660–690 nm, ATX-106, and indocyanine green (ICG). Another photosensitive agent that may be used is verteporfin, a synthetic, chlorin-like porphyrin. It may be activated at a wavelength of around 689 nm. Once activated, it generates singlet oxygen and other reactive oxygen radicals that selectively damage tissues.

A composition may be prepared that contains two of compound 2 and thus the composition may function as a dual functional agent. That is, the composition has one compound 2 with a component capable of photodiagnosis, with the other compound 2 having a component capable of phototherapy. For example, a phototherapeutic Dye in one compound may be a member of the porphyrin class of compounds, or a member of the phenoxazines, phenothiazines, etc. class of compounds. This compound of the composition will provide phototherapy upon activated, as described using porphyrins as a representative but nonlimiting example. The Dye in the other compound may be a member of the cyanine, indocyanine, fluorescein, etc. class of compounds.

A component selected as Dye or Y that is cationic carries a positive charge on the heteroatoms of the ring structure. Cationic dyes tend to be bound intracellularly, with some dyes such as rhodamine being selectively taken up by mitochondria of living cells. A component selected as Dye or Y that is not cationic may be attached to polycationic peptides to facilitate intracellular intake. Such polycationic peptides include polymyxin-B nonapeptide and poly-L-lysine.

Cationic dyes such as methylene blue, rhodamine and analogues of chalcogenopyryliums, may have one of their core oxygen or nitrogen atoms replaced by a heavy atom, such as tellurium or selenium. In addition, phthalocyanine and naphthalocyanine dyes may contain a diamagnetic metal such as aluminum, zinc, or tin, within the center of their ring structure. Such replacements are expected to yield a long-lived triplet state of the activated compound which, in turn, should enhance the photodynamic therapy (PDT) effect of the Dye.

In one embodiment of either compound 1 or compound 2, the Dye and/or Y is an aromatic or a heteroaromatic radical derived from or in the class of any of cyanines, phthalocyanines, porphyrins, indocyanines, rhodamines, phenoxazines, phenothiazines, phenoselenazines, fluoresceins, benzoporphyrins, squaraines, corrins, azo dyes, diazo dyes, croconiums, chalcogenopyrylium analogues, non-cationic dyes attached to polycationic peptides; chlorines, naphthalocyanines, non-cationic dyes attached to polycationic peptides, cationic dyes, methine dyes, and indolenium dyes; E is either hydrogen or selected from the group of somatostatin receptor binding molecules, heat sensitive bacterioendotoxin (ST) receptor binding molecules, neurotensin receptor binding molecules, bombesin receptor binding molecules, cholecystekinin (CCK) receptor binding molecules, steroid receptor binding molecules, and carbohydrate receptor binding molecules; L is selected from the group consisting of —HNCO—, —CONR$^1$—, —HNCONH—, —HNCSNH—, —HNNHCO—, —(CH$_2$)$_a$CONR$^1$—, —CONR$^1$(CH$_2$)$_a$NR$^2$CO—, and —NR$^1$CO(CH$_2$)$_a$CONR$^2$—; R$^1$ and R$^2$ are independently selected from the group consisting of hydrogen, C1–C10 alkyl, C1–C10 polyhydroxyalkyl; and a, b, and c independently range from 0 to 6.

In an alternative embodiment of either compound 1 or compound 2, the Dye is an aromatic or a heteroaromatic radical derived from or in the class of cyanines, phthalocyanines, rhodamines, porphyrins, benzoporphyrins, corrins; Y may be hydrogen, halogens, anthracylines, azides, C1–C20 peroxyalkyl, C1–C20 peroxyaryl, C1–C20 sulfenatoalkyl, sulfenatoaryl, an aromatic or a heteroaromatic radical derived from or in the class of any of cyanines, phthalocyanines, porphyrins, indocyanines, rhodamines, phenoxazines, phenothiazines, phenoselenazines, fluoresceins, benzoporphyrins, squaraines, corrins, azo dyes, diazo dyes, croconiums, chalcogenopyrylium analogues, non-cationic dyes attached to polycationic peptides; chlorines, naphthalocyanines, cationic dyes, methine dyes, and indolenium dyes; E is selected from the group of octreotide and octreotate peptides, heat-sensitive bacterioendotoxin receptor binding peptides, carcinoembryonic antigen antibody (anti-CEA), bombesin receptor binding peptide, neurotensin receptor binding peptide, cholecystekinin receptor binding peptide, and estrogen steroids; L is selected from the group of —HNCO—, —CONR$^1$—, —HNCSNH—, —HNNHCO—, —(CH$_2$)$_a$CONR$^1$—, —CONR$^1$(CH$_2$)$_a$NR$^2$CO—, and R$^1$ and R$^2$ are independently selected from the group consisting of hydrogen, C1–C10 alkyl, C1–C5 polyhydroxyalkyl; and a, b, and c independently range from 0 to 6.

These compounds operate by a dual mechanism as shown in FIG. 1. Type I agents generate reactive intermediates such as free radicals directly upon photoexcitation and do not require oxygen. Type II agents generate singlet oxygen by energy transfer from photoexcited dyes to oxygen in tissues.

Type I agents contain a labile precursor that undergoes photofragmentation upon direct irradiation with the light of desired wavelength, and produces reactive intermediates such as nitrenes, carbenes, or free radicals. For example, azides (R—$N_3$) produce nitrenes (R—N:); diazoalkanes (R—$CHN_2$) produce carbenes (R—CH:); peroxides (RO—OR) produces alkoxy radicals (RO.); alkyl iodides (R—I) produces alkyl radicals (R.); and sulfenates (RS—OR) produces alkoxy radicals (RO.) and mercapto radicals (RS.). Alternatively, the reactive intermediates can also be produced indirectly by exciting an aromatic chromophore (e.g. the Dye component and the excited Dye can transfer the energy intramolecularly to the azide and cause fragmentation). Upon photoexcitation, Type II agents generate a singlet oxygen from the normal triplet oxygen that is present in the tissues upon photoexcitation of a Dye. This is followed by collisional energy transfer from the excited Dye to the oxygen. Energy transfer is the most efficient when the Dye has absorption maxima at about 650 nm (red light), but decreases substantially at other wavelengths. Phenoxazines, phenothiazines, and phenoselanazines may also operate by either the Type I mechanism or Type II mechanism, depending upon the wavelength of light that is use in a procedure.

Aliphatic azido compounds can also be used for phototherapy, but may require high-energy light for activation unless the azide moiety is attached to a conjugated polyene system.

The Dye component is linked via linker L to a moiety that can be used to target the compound. The targeting moiety E may include steroid hormones for the treatment of breast and prostate lesions; whole or fragmented somatostatin, bombesin, and neurotensin receptor binding molecules for the treatment of neuroendocrine tumors; whole or fragmented cholecystekinin (CCK) receptor binding molecules for the treatment of lung cancer; whole or fragmented heat sensitive bacterioendotoxin (ST) receptor and carcinoembryonic antigen (CEA) binding molecules for the treatment of colorectal cancer, dihyroxyindolecarboxylic acid and other melanin producing biosynthetic intermediates for melanoma; whole or fragmented integrin receptor and atherosclerotic plaque binding molecules for the treatment of vascular diseases; and whole or fragmented amyloid plaque binding molecules for the treatment of brain lesions. The targeting moiety may have one or more particular regions termed an epitope, that is recognized by and binds to, the target site on the cell.

These targeting moieties may be associated with, that is, be part of a biomolecule, which include hormones, amino acids, peptides, peptidomimetics, proteins, nucleosides, nucleotides, nucleic acids, enzymes, carbohydrates, glycomimetics, lipids, albumins, whole or fragmented mono- and polyclonal antibodies, receptors, inclusion compounds such as cyclodextrins, and receptor binding molecules. Biomolecules for use in the present invention may also include synthetic polymers. Examples of synthetic polymers include polyaminoacids, polyols, polyamines, polyacids, oligonucleotides, aborols, dendrimers, and aptamers. Coupling of diagnostic and radiotherapeutic agents to biomolecules can be accomplished by methods well known in the art, as disclosed in Hnatowich et al., *Radioactive Labeling of Antibody: A simple and efficient method. Science,* 1983, 220, 613–615; A. Pelegrin et al., *Photoimmunodiagnosis with antibody-fluorescein conjugates: in vitro and in vivo preclinical studies. Journal of Cellular Pharmacology,* 1992, 3, 141–145; and U.S. Pat. No. 5,714,342, each of which is expressly incorporated by reference herein in its entirety.

Successful specific targeting of fluorescent dyes to tumors using antibodies and peptides for diagnostic imaging of tumors has been demonstrated by us and others, for example, in S. A. Achilefu et al., *Novel receptor-targeted fluorescent contrast agents for in vivo tumor imaging,* Investigative Radiology, 2000, 35(8), 479–485; B. Ballou et al., *Tumor labeling in vivo using cyanine-conjugated monoclonal antibodies. Cancer Immunology and Immunotherapy,* 1995, 41, 257–263; and K. Licha et al., *New contrast agents for optical imaging: acid-cleavable conjugates of cyanine dyes with biomolecules. In Biomedical Imaging: Reporters, Dyes, and Instrumentation,* D. J. Bornhop, C. Contag, and E. M. Sevick-Muraca (Eds.), Proceedings of SPIE, 1999, 3600, 29–35, each of which is expressly incorporated by reference herein in its entirety. Therefore, the inventive receptor-targeted phototherapeutic agents are expected to be effective in the treatment of various lesions.

In the present invention, dual phototherapeutic effect involving both Type I and Type II mechanisms can be accomplished by incorporating the reactive intermediate precursors into a conventional PDT dye and using a dual wavelength light source to effect the generation of reactive intermediates as well as the generation of singlet oxygen. In some cases it may be possible to activate both Type I and Type II mechanisms using same wavelength of light. Dyes containing azide group have been prepared previously, as in S. Sunthankar et al., *Reactive disperse dyes. 1. Reactivity involving nitrene intermediate from azido group. Indian Journal of Chemistry,* 1973, 11(5), 503–504, which is expressly incorporated by reference herein in its entirety.

In the process outlined in FIG. 1, photoexcitation of the aromatic chromophore effects rapid intramolecular energy transfer to the azido group, resulting in bond rupture and production of nitrene and molecular nitrogen. The nitrogen that is released is in a vibrationally excited state, which may cause additional cellular injury.

For targeting purposes, external attachment of a targeting moiety is used. If the aromatic azido compounds themselves preferentially accumulate in the target tissue, however, an additional binding group may not be needed. For example, if Y is an anthracycline moiety, it will bind to cancer cells directly and would not require an epitope for targeting purposes. While anthracycline compounds do not have an azide group, photoexcitation produces a free radical for a Type I mechanism.

Figure 2:
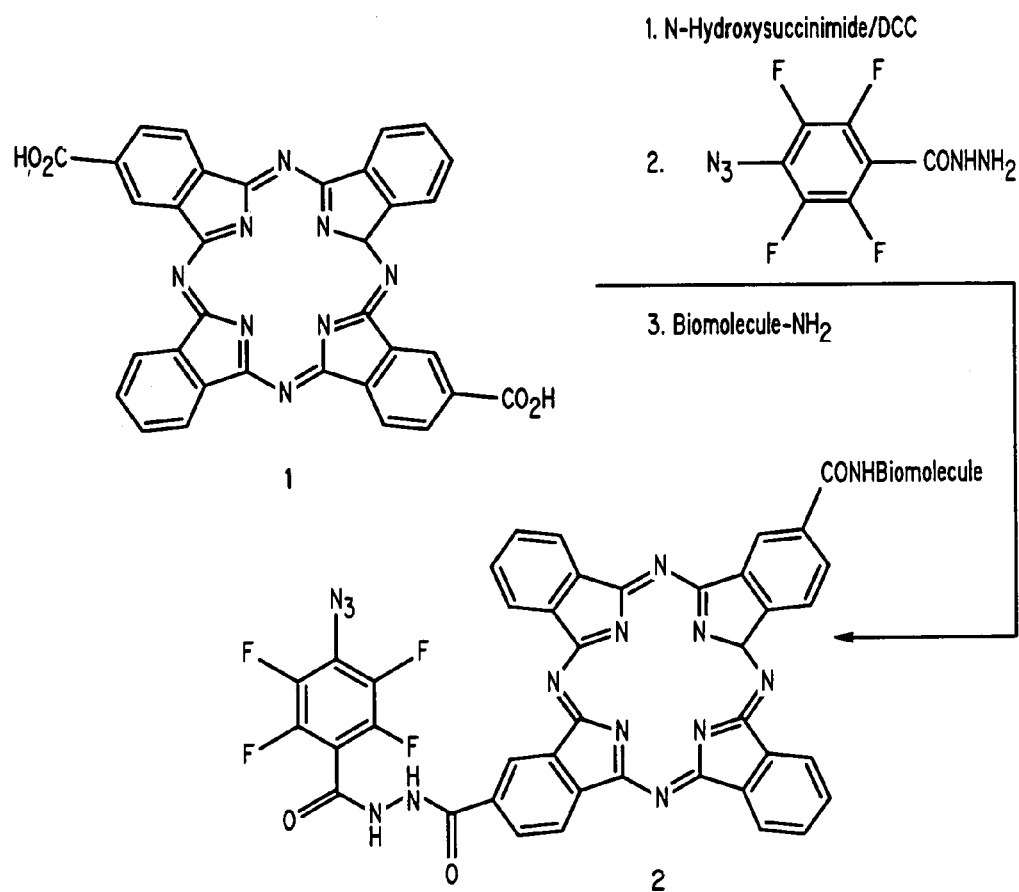
FIG. 2 is a schematic mechanism for the synthesis of a phthalocyanine derivative.
Figure 3:
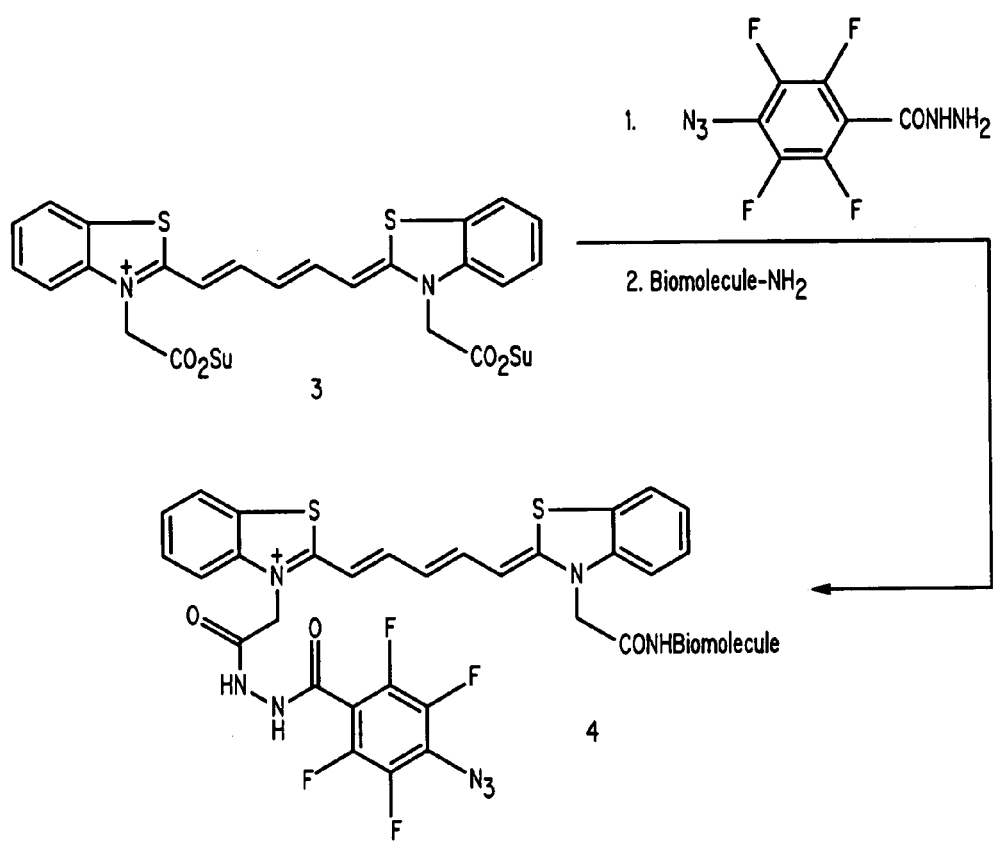
FIG. 3 is a schematic mechanism for the synthesis of a cyanine derivative.

The Dye-azide derivatives of the present invention contain additional functionalities that can be used to attach various types of biomolecules, synthetic polymers, and organized aggregates for selective delivery to various organs or tissues of interest. The synthesis of typical dual phototherapeutic agents incorporating both Type 1 and Type 2 mechanisms based on phthalocyanine and cyanine derivatives, as examples, are shown in FIGS. 2 and 3 respectively. Referring to FIG. 2, the diacid 1 can be prepared by the method analogous to phthalocyanine itself described previously in J. E. van Lier and J. D. Spikes, *The chemistry, photophysics, and photosensitizing properties of phthalocyanines, In Photosensitizing Compounds: Their Chemistry, Biology, and Clinical Use* (Ciba Foundation Symposium 146), G. Bock and S. Harnett (Eds.), J. Wiley & Sons, 1989, pp. 17–32, which is expressly incorporated by reference herein its entirety. The diacid 1 can be converted to the corresponding bis active ester in which one of the active esters can be condensed with an azide (by the Type 1 moiety) and the other active ester can be condensed with a biomolecule of interest to yield the phthalocyanine derivative 2. Referring to FIG. 3, the cyanine dye 3 is prepared by the alkylation of 2-methylbenzothiazole with N-succinimydyl bromoacetate followed by condensation with malonaldehyde tetramethyl acetal. One of the active esters in the cyanine Dye 3 can be attached to a Type 1 moiety and the other ester can be attached to a biomolecule to give the dual photherapeutic agent 4. Specifically, the biomolecules bind to colorectal, cervical, ovarian, lung, and neuroendocrine tumors, and include somatostatin, cholecystekinin, bombesin, neuroendrocrine, and heat sensitive bacterioendotoxin receptor binding compounds. The other active ester can be conjugated to an aromatic or an aliphatic azides depending on the wavelength desired for excitation.

The novel compounds of the present invention may vary widely depending on the contemplated application. For tumor targeting, the targeting moiety is selected from the class of tumor markers including, but not limited to, whole or fragmented somatostatin, bombesin, neurotensin, cholecystekinin, heat sensitive bacterioendotoxin, estrogen, and progesterone receptor binding compounds. For vascular lesions, the targeting moiety may be selected from the class of integrins, selectins, vascular endothelial growth factor, fibrins, tissue plasminogen activator, thrombin, LDL, HDL, Sialyl Lewis$^x$ and its mimics, and atherosclerotic plaque binding compounds.

Methods of performing therapeutic procedures with the inventive compound are also disclosed. An effective amount of the inventive compound in a pharmaceutically acceptable formulation is administered to a patient. For example, parenteral administration advantageously contains a sterile aqueous solution or suspension of the photosensitizer in a concentration ranging from about 1 nM to about 0.5 M. In various embodiments parenteral formulations may have a concentration of 1 μM to 10 mM photosensitizer. Such solutions also may contain pharmaceutically acceptable buffers, emulsifiers, surfactants, and, optionally, electrolytes such as sodium chloride. Formulations for enteral administration may vary widely, as is well known in the art. In general, such formulations are liquids, which include an effective amount of the complexes in aqueous solution or suspension. Such enteral formulations may optionally include buffers, surfactants, emulsifiers, thixotropic agents, and the like. Compounds for oral administration may also contain flavoring agents and other ingredients for enhancing their organoleptic qualities. Formulations for topical delivery may also contain liquid or semisolid excipients to assist in the penetration of the photosensitizer. The compounds may also be delivered in an aerosol spray. The dose of the photosensitizer may vary from 0.1 to 500 mg/kg body weight, preferably from 0.5 to 2 mg/kg body weight. The photosensitizer is allowed to accumulate in the region of interest, followed by illumination with the light of wavelength 300 to 1200 nm, preferably 350 to 850 nm, at the site of the lesion. If the lesion is on the skin surface, the photosensitizer can be directly illuminated; otherwise, endoscopic catheters equipped with a light source may be employed to achieve phototherapeutic effect. The intensity, power, duration of illumination, and the wavelength of the light may vary widely depending on the location and site of the lesions. The fluence rate is preferably, but not always, kept below 200 mW/cm$^2$ to minimize thermal effects. Appropriate power depends on the size, depth, and the pathology of the lesion. The inventive compounds have broad clinical utility which includes, but is not limited to, phototherapy of tumors, inflammatory processes, and impaired vasculature.

The Dye containing compounds can also be used both as a diagnostic agent as well as a photodynamic therapeutic agent concomitantly. For example, an effective amount of the inventive compound in a pharmaceutically acceptable formulation is administered to a patient, as previously described for the method of performing a phototherapeutic procedure. Administration is followed by a procedure that combines photodiagnosis and phototherapy. For example a composition comprising compounds for combined photodiagnosis and phototherapy is administered to a patient and its concentration, localization, or other parameters is determined at the target site of interest. More than one measurement may be taken to determine the location of the target site. The time it takes for the compound to accumulate at the target site depends upon factors such as pharmcokinetics, and may range from about thirty minutes to two days. Once the site is identified, the phototherapeutic part of the procedure may be done either immediately after determining the site or before the agent is cleared from the site. Clearance depends upon factors such as pharmacokinetics, type of tissue (e.g. lipid stores), etc.

The inventive compounds can be formulated into diagnostic or therapeutic compounds for enteral, parenteral, topical, aerosol, inhalation, or cutaneous administration. Topical or cutaneous delivery of the photosensitizer may also include aerosol formulation, creams, gels, solutions, etc. The compounds are administered in doses effective to achieve the desired diagnostic or therapeutic effect. Such doses may vary widely depending upon the particular compounds employed in the composition, the organs or tissues to be examined, the equipment employed in the clinical procedure, the efficacy of the treatment achieved, and the like. These compositions contain an effective amount of the compound(s), along with conventional pharmaceutical carriers and excipients appropriate for the type of administration contemplated. These compostions may also include stabilizing agents and skin penetration enhancing agents.

In another embodiment, the photodiagnostic and phototherapeutic agents may be formulated as micelles, liposomes, microcapsules, or other microparticles. These formulations may enhance delivery, localization, target specificity, administration, etc. As one example, a liposome formulation of the inventive composition(s) may be beneficial when the compound does not contain a specific targeting moiety (e.g., when E is hydrogen). As another example, a liposome formulation of the inventive compound(s) may be beneficial when the compound(s) have solubility limitations. Preparation and loading of these are well known in the art.

As one example, liposomes may be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, *Liposome Dermatics*, Springer-Verlag, Berlin (1992)). Polycaprolactone, poly(glycolic) acid, poly(lactic) acid, polyanhydride or lipids may be formulated as microspheres. As an illustrative example, the optical agent may be mixed with polyvinyl alcohol (PVA), the mixture then dried and coated with ethylene vinyl acetate, then cooled again with PVA. In a liposome, the optical agent may be within one or both lipid bilayers, in the aqueous between the bilayers, or with the center or core. Liposomes may be modified with other molecules and lipids to form a cationic liposome. Liposomes may also be modified with lipids to render their surface more hydrophilic which increases their circulation time in the bloodstream. The thus-modified liposome has been termed a "stealth" liposome, or a long-lived liposome, as described in U.S. Pat. Nos. 6,277,403; 6,610,322; 5,631,018; 5,395,619; and 6,258,378, each of which is expressly incorporated by reference herein in its entirety, and in *Stealth Liposomes*, Lasic and Martin (Eds.) 1995, CRC Press, London, specifically pages. Encapsulation methods include detergent dialysis, freeze drying, film forming, injection, as known to one skilled in the art and disclosed in, for example, U.S. Pat. No. 6,406,713 which is expressly incorporated by reference herein in its entirety.

The compound formulated in liposomes, microcapsules, etc. may be administered by any of the routes previously described. In a formulation applied topically, the optical agent is slowly released over time. In an injectable formulation, the liposome capsule circulates in the bloodstream and is delivered to a desired site. The use of liposomes, microcapsules, or other microparticles allows the incorporation of two or more of the inventive compound of different types and capabilities in the composition.

The compound could be also used as antimicrobial agents and used for the treatment of infections, wounds, and burn healing, as described by Hamblin et al., in "Targeted photodynamic therapy for infected wounds in mice" in *Optical Methods for Tumor Treatment and Detection: Mechanisms and Techniques in Photodynamic Tharapy XI* (Proceedings of SPIE 2002) which is expressly incorporated by reference herein in its entirety. In this regard, the use of liposomes etc., as delivery vehicles for the compounds would be desired.

For example, formula 1, formula 2, or both, having any neutral or anionic dyes, in combination with cationic dyes or photosensitizers, such as those for chlorins, porphyrins, phtahalocyanines, and phenothiazines in their DYE or Y components, are partially or totally encapsulated in a liposome or other microparticle. The E component of either formula may be a hydrogen or a targeting moiety as previously described. The compound(s) is administered to a patient and is localized at an infected site. A photodiagnostic and phototherapeutic procedure is performed to detect the compound at the infected site and subsequently treat the infected area by activating the compounds to kill the infectious agent.

The following example illustrates one non-limiting embodiment of the invention pertaining to the preparation and properties of a typical bioconjugate derived from bombesin, a bioactive peptide; 4-azido-2,3,5,6-tetrafluorophenylbenzoyl hydrazide, a Type I chromophore; and carboxymethylcyanine dye, a PDT chromophore. The above-listed compounds are well known to those skilled in the art and general descriptions of the compounds and their synthesis are described in U.S. Pat. No. 6,180,085; Jori, G., *Far-red-absorbing photosensitizers: their use in the photodynamic therapy of tumours*, J. Photochem. Photobiol. A: Chem., 62, (1992), 371–378; Patonay, G. and M. Antoine, *Near-Infrared Fluorogenic Labels: New Approach to an Old Problem*, Anal. Chem., 63:6, (1991) 321A–327A; and Jori, G. and E. Reddi, *Second Generation Photosensitizers for the Photodynamic Therapy of Tumours*, in *Light in Biology and Medicine*, Volume 2 (ed. R. H. Douglas et al.), Plenum Press, New York, (1991), 253–266, the disclosures of which are herein incorporated by reference in their entireties.

As would be apparent to skilled artisans, various changes and modifications are possible and are contemplated within the scope of the invention described. It should be understood that the embodiments of the present invention shown and described in the specification are only specific embodiments of the inventors, who are skilled in the art, and are not limiting in any way. Therefore, various changes, modifications or alterations to those embodiments may be made or resorted to without departing from the spirit of the invention and the scope of the following claims. For example, although the compounds of the present invention are primarily directed at therapy, most of the compounds containing polycyclic aromatic chromophores can also be used for optical diagnostic imaging purposes.

What is claimed is:

1. A photoactive composition comprising a pharmaceutically acceptable formulation of compound of E-L-DYE-X—$N_3$(formula 1) where
    DYE is selected from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, and indolenium dyes,
    E is selected from the group consisting of somatostatin receptor binding molecules, heat sensitive bacterioendotoxin receptor binding molecules, neurotensin receptor binding molecules, bombesin receptor binding molecules, cholesystekinin receptor binding molecules, steroid receptor binding molecules, carbohydrate receptor binding molecules;
    L is selected from the group consisting of —$(CH_2)_a$—, —$(CH_2)_b CONR^1$—, —$N(R^2)CO(CH_2)_c$—, —$OCO(CH_2)_d$—, $(CH_2)_e CO_2$—, —$OCONH$—, —$OCO_2$—, —$HNCONH$—, —$HNCSNH$—, —$HNNHCO$—, —$OSO_2$—, —$NR^3(CH_2)_e CONR^4$—, —$CONR^5(CH_2)_f NR^6 CO$—, and —$NR^7 CO(CH_2)_g CONR^8$—;
    X is either a single bond or is selected from the group consisting of —$(CH_2)_h$—, —$OCO$—, —$HNCO$—, —$(CH_2)_i CO$—, and —$(CH_2)_j OCO$—;
    $R^1$ to $R^8$ are independently selected from the group consisting of hydrogen, C1–C10 alkyl, —OH, C1–C10 polyhydroxyalkyl, C1-C10 alkoxyl, C1-C10 alkoxyalkyl, —$SO_3H$, —$(CH_2)_k CO_2 H$, and —$(CH_2)_l NR^9 R^{10}$;
    $R^9$ and $R^{10}$ are independently selected from the group consisting of hydrogen, C1–C10 alkyl, C5–C10 aryl, and C1–C10 polyhydroxyalkyl; and a to l independently range from 0 to 10, as a photosensitive composition.

2. The composition of claim 1 comprising at least two of formula 1.

3. The composition of claim 1 further comprising a diamagnetic metal coordinated with a phthalocyanine or naphthalocyanine.

4. The composition of claim 1 wherein the Dye is bonded with a polycationic peptide.

5. The composition of claim 1 further comprising at least one of tellurium or selenium replacing a core oxygen or nitrogen in a Dye selected from the group consisting of rhodamine, methylene blue, and a chalcogenopyrylium analogue.

6. A compound comprising formula 1

E-L-DYE-X—$N_3$ where
    DYE is selected from at least one of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, and indolenium dyes,
    E is selected from the group consisting of somatostatin receptor binding molecules, heat sensitive bacterioendotoxin receptor binding molecules, neurotensin receptor binding molecules, bombesin receptor binding molecules, cholesystekinin receptor binding molecules, steroid receptor binding molecules, and carbohydrate receptor binding molecules;

L is selected from the group consisting of —$(CH_2)_a$—, —$(CH_2)_b CONR^1$—, —$N(R^2)CO(CH_2)_c$—, —$OCO(CH_2)_d$—, —$(CH_2)_e CO_2$—, —OCONH—, —$OCO_2$—, —HNCONH—, —HNCSNH—, —HNNHCO—, —$OSO_2$—, —$NR^3(CH_2)_e CONR^4$—, —$CONR^5(CH_2)_f NR^6 CO$—, and —$NR^7 CO(CH_2)_g CONR^8$—;

X is either a single bond or is selected from the group consisting of —$(CH_2)_h$—, —OCO—, —HNCO—, —$(CH_2)_i CO$—, and —$(CH_2)_j OCO$—;

$R^1$ to $R^8$ are independently selected from the group consisting of hydrogen, C1–C10 alkyl, —OH, C1–C10 polyhydroxyalkyl, C1–C10 alkoxyl, C1–C10 alkoxyalkyl, —$SO_3H$, —$(CH_2)_k CO_2 H$, and —$(CH_2)_l NR^9 R^{10}$;

$R^9$ and $R^{10}$ are independently selected from the group consisting of hydrogen, C1–C10 alkyl, C5–C10 aryl, and Ci-ClO polyhydroxyalkyl; and a to l independently range from 0 to 10.

7. The compound of claim 6 formulated in a liposome.

* * * * *

UNITED STATES PATENT AND TRADEMARK OFFICE
CERTIFICATE OF CORRECTION

PATENT NO. : 7,230,088 B2  
APPLICATION NO. : 10/685172  
DATED : June 12, 2007  
INVENTOR(S) : Raghavan Rajagopalan et al.

Page 1 of 1

It is certified that error appears in the above-identified patent and that said Letters Patent is hereby corrected as shown below:

COLUMN 18  
Line 29, "$(CH_2)_eCO_2$—," should read ---$(CH_2)_eCO_2$—,--.

COLUMN 19  
Line 11, "$CONR^4$," should read --$CONR^4$-,--.

COLUMN 20  
Line 10, "Ci-C1O" should read --C1-C10--.

Signed and Sealed this

Twenty-ninth Day of April, 2008

JON W. DUDAS  
*Director of the United States Patent and Trademark Office*